United States Patent [19]
Hering et al.

[11] Patent Number: 5,553,177
[45] Date of Patent: Sep. 3, 1996

[54] OPTICAL FIBER DEVICE WHICH INCREASES LIGHT INTENSITY

[75] Inventors: Peter Hering, Garching; Michael Haisch, Munich, both of Germany

[73] Assignee: CeramOptec Industries, Inc., East Longmeadow, Mass.

[21] Appl. No.: 274,912

[22] Filed: Jul. 14, 1994

[30] Foreign Application Priority Data

Jan. 15, 1992 [DE] Germany .................. 4200887C1
Jan. 14, 1993 [WO] WIPO .................. PCT/DE93/00022

[51] Int. Cl.$^6$ .................. G02B 6/26; F21V 7/04
[52] U.S. Cl. .................. 385/31; 385/32; 385/38; 385/123; 385/147; 385/901; 362/32
[58] Field of Search .................. 385/14, 15, 31, 385/32, 38, 123, 147, 901; 362/32

[56] References Cited

U.S. PATENT DOCUMENTS

| | | | |
|---|---|---|---|
| 4,011,403 | 3/1977 | Epstein et al. | 385/901 X |
| 4,500,164 | 2/1985 | Kiyohara | 385/43 X |
| 4,804,323 | 2/1989 | Kim | 385/901 X |
| 5,042,892 | 8/1991 | Chiu et al. | 385/114 |
| 5,042,894 | 8/1991 | Swemer | 385/33 |
| 5,367,440 | 11/1994 | Gruszczynski et al. | 362/32 |

FOREIGN PATENT DOCUMENTS

| | | | |
|---|---|---|---|
| 2607249 | 8/1977 | Germany | 385/901 X |
| 2808045 | 9/1979 | Germany | 385/901 X |
| 3644839 | 6/1988 | Germany | 385/901 X |
| 3009171 | 2/1989 | Germany | 385/901 X |

*Primary Examiner*—Brian Healy
*Attorney, Agent, or Firm*—Bolesh J. Skutnik

[57] ABSTRACT

A lightguiding device, which can be an integral part of a lightguiding system, can increase the light intensity exiting from a lightguide by concentrating the transmitted light into a small portion of the lightguide's cross section. The device consists of a section of a lightguiding material which has been bent at an angle greater than 45 degrees relative to the axis of light transmission, preferably at an angle of 90 degrees with a small bend radius. In the bent section, a homogeneous refractive index is required at least for the lightguide's core. The lightguide must be terminated immediately beyond the bent section. Alternatively, a preformed bent section of appropriate lightguiding material can be attached to an end of a straight section of lightguide to increase the exiting light intensity. All types of lightguiding systems can be used to enhance output intensities, including glass or pure silica lightguides, hollow waveguides, liquid core lightguides and plastic lightguides. It is possible to provide exiting light of increased intensity across the full electromagnetic spectrum from UV to IR through selection of appropriate lightguiding materials.

19 Claims, 1 Drawing Sheet

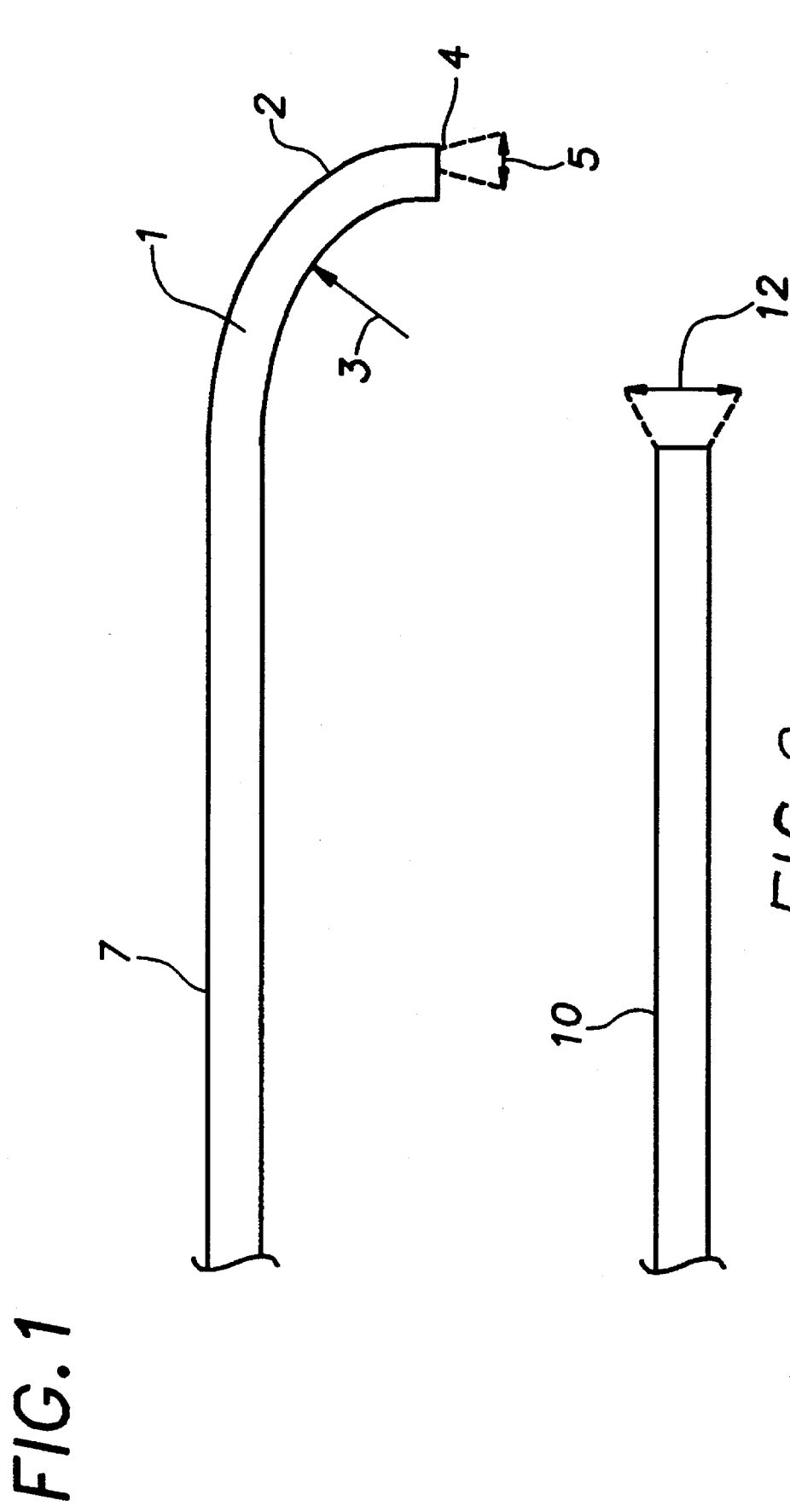

OPTICAL FIBER DEVICE WHICH INCREASES LIGHT INTENSITY

BACKGROUND OF INVENTION

The field of the present invention is lightguiding devices which can increase the light intensity at the end of a lightguide.

A typical lightguide consists of a core section, which carries a light signal, and a clad section over the core section. It is known in the state of the art to increase the light intensity exiting from a lightguide by placement of lenses and other objects on the lightguide's end. Alternatively a tapered lightguide can be employed to achieve an increased intensity at the output end.

Both solutions have problems. Attaching optical devices to the lightguide's end can be difficult and expensive to accomplish. The manufacture of tapered lightguides is also demanding and thus costly. Additionally tapered lightguides can not be manufactured from all kinds of materials.

BRIEF SUMMARY OF THE INVENTION

It is thus an object of the invention to provide a simple lightguiding device which overcomes the drawbacks of the prior art.

It is a further object of the invention to provide a lightguiding device which increases the light intensity exiting from a lightguide so as to enhance the power density for laser surgery or to better illuminate objects under observation.

Briefly stated, a lightguiding device, which can be an integral part of a lightguiding system, can increase the light intensity exiting from a lightguide by concentrating the transmitted light into a small portion of the lightguide's cross section. The device consists of a section of a lightguiding material which has been bent at an angle greater than 45 degrees relative to the axis of light transmission, preferably at an angle of 90 degrees with a small bend radius. In the bent section, a homogeneous refractive index is required at least for the lightguide's core. The lightguide must be terminated immediately beyond the bent section. Alternatively, a preformed bent section of appropriate lightguiding material can be attached to an end of a straight lightguide section to increase the exiting light intensity. All types of lightguiding systems can be used to enhance output intensities, including glass or pure silica lightguides, hollow waveguides, liquid core lightguides and plastic lightguides. It is possible to provide exiting light of increased intensity across the full electromagnetic spectrum from UV to IR through a selection of appropriate lightguiding materials.

It should be emphasized that merely bending a section of a lightguide in the normal fashion, as e.g. in German patents DE-PS 30 09 171; DE-OS 28 08 045; or DE-OS 29 07 249, is not adequate to obtain the benefits of the present invention. Typically in the state of the art devices, a lightguide is bent primarily to facilitate access to hard-to-reach places.

The key elements of the present invention are a sharply bent section of a lightguide in which a homogeneous refractive index is maintained at least over a lightguide's core in the bent section. Effectively this means stresses are not permitted to be present in a bent lightguide section of this invention. Further the focusing effect is a short range feature, thus a lightguide must be terminated immediately after the bent section.

The above, and other objects, features and advantages of the present invention will become apparent from the following description read in conjunction with the accompanying drawing.

BRIEF DESCRIPTION OF THE DRAWING

In FIG. 1, a lightguiding device of the present invention is compared with a standard state of the art optical lightguide, shown in FIG. 2.

DETAILED DESCRIPTION OF PREFERRED EMBODIMENTS

Referring to FIG. 1, a lightguide device 1 consists of a bent section 2 with a small bend radius 3 at an end of a lightguide 7. Lightguide device 1 terminates immediately after bent section 2. Light 4 exits lightguide device 1 in a tighter spatial distribution 5 and concentrated to the outside of the bend, as shown. A higher energy density of the exiting light is observed than from a standard straight lightguide 10 of the prior art depicted at the bottom of FIG. 1. With a straight lightguide 10, light exits its end in a broad spatial distribution 12, exiting from the entire surface of lightguide 10.

Bent section 2 must be stress free so that a homogeneous refractive index is maintained over a core section of lightguide device 1. Bent section 2 can be made stress free if its material has thermoplastic characteristics by an application of a thermal annealing treatment after creation of the bend.

An angle greater than 45 to 60 degrees is preferred. In particular, as shown in FIG. 1, an angle of 90 degrees is especially preferred and useful for dental applications.

Bend radius 3 of bent section 2 should be as small as possible. Further since bend losses increase rapidly with decreasing bend radius, it is useful to choose a numerical aperture of lightguiding device 1 to be equal to that of preceding straight lightguide section 7. Preferably, the numerical aperture of bent section 2 would be greater than that of straight lightguide section 7.

In one experiment, a number of bent glass rods were prepared. A CCD camera was used to measure the intensity profile from the bent rods. The total light energy output was observed to exit from about ¼ of each glass rod's end surface.

If the numerical aperture of each section of the device, the angle of bend, the bend radius and the distribution of light entering the device are known, one can calculate the expected increase in light intensity, for example by ray tracing.

In another embodiment of the invention, a bent piece can be made independently and then attached to an end of a straight lightguide. An example of this embodiment is a glass rod of cross sectional area approximately equal to that a lightguide. A stress free glass rod can be made by using a flame to create a bend and then using the flame to temper the bent glass rod. A relatively high numerical aperture is obtained if the glass rod is surrounded by air or water only. Alternatively, a relatively high numerical aperture can be obtained by mirror coating of the glass rod.

Another method of creating a stress free bent piece of lightguiding material is by forming a bent shape from molten material. In this method a mold is prepared. Material is melted and then poured into the mold. With an appropriate cooling cycle, a stress free bent lightguide device is produced.

Another embodiment of the invention would be to use a bent lightguide device with a liquid core. In this case, it is critical that as thin a closing section as possible be used for the end where light is to exit in operation. In similar fashion, hollow lightguides or waveguides in which light waves are guided by metallic or dielectric reflections may also be used to enhance light intensity exiting from such systems.

Having described preferred embodiments of the invention with reference to the accompanying drawing, it is to be understood that the invention is not limited to those precise embodiments, and that various changes and modifications may be effected therein by one skilled in the art without departing from the scope or spirit of the invention as defined in the appended claims.

What is claimed is:

1. A lightguiding device which increases the light intensity exiting from its distal end, comprising:

a bent lightguide section being at an end of a lightguide having a diameter, a core section and a clad section, and having a bend angle and a bend radius;

said bend radius being as small as possible without exceeding said fiber's waveguiding limit;

said bent lightguide section, being stress free, and having a homogeneous refractive index throughout said core section;

said bent lightguide section and straight lightguide section having numerical apertures; and said bent lightguide section being an integral part of a preceding straight lightguide.

2. A device according to claim 1, wherein said bend angle is greater than 45 degrees, and preferably exactly 90 degrees.

3. A device according to claim 1, wherein said numerical aperture of said bent lightguide section is equal to or greater than that of said straight lightguide section.

4. A device according to claim 1, wherein said bent lightguide section is formed by heat treatment of a thermoplastic material to produce a homogeneous refractive index in its core section.

5. A device according to claim 1, wherein said bent lightguide section is tempered after formation of said bend angle.

6. A device according to claim 1, wherein said bent lightguide section is either a glass or quartz rod.

7. A device according to claim 6, wherein said rod is surrounded by air or by water or it is mirror coated.

8. A device according to claim 1, wherein said bent lightguide section is a hollow lightguide which uses either metallic or dielectric reflections for waveguiding.

9. A device according to claim 1, wherein said bent lightguide section is a hollow lightguide, said core section is liquid, and a thin walled closure is used at said distal end.

10. A lightguiding device which increases the light intensity exiting from its distal end, comprising:

a bent lightguide section having a diameter and having a core section and a clad section;

said bent lightguide section with as small a bend radius as possible without exceeding said fiber's waveguiding limit, forming said distal end of said lightguiding device;

said bent lightguide section, being stress free, and having a homogeneous refractive index throughout said core section;

said bent lightguide section and straight lightguide section having numerical apertures; and said bent lightguide section being a separate bent piece attached to a preceding lightguide.

11. A device according to claim 10, wherein said bend angle is greater than 45 degrees, and preferably exactly 90 degrees.

12. A device according to claim 10, wherein said numerical aperture of said bent lightguide section is equal to or greater than that of said straight lightguide section.

13. A device according to claim 10, wherein said bent lightguide section is formed by heat treatment of a thermoplastic material to produce a homogeneous refractive index in its core section.

14. A device according to claim 10, wherein said bent lightguide section is tempered after formation of said bend angle.

15. A device according to claim 10, wherein said bent lightguide section is either a glass or quartz rod.

16. A device according to claim 15, wherein said rod is surrounded by air or by water or it is mirror coated.

17. A device according to claim 10, wherein said bent lightguide section is a hollow lightguide which uses either metallic or dielectric reflections for waveguiding.

18. A device according to claim 10, wherein said bent lightguide section is a hollow lightguide, said core section is liquid, and a thin walled closure is used at said exiting end.

19. A device according to claim 10, wherein said bent lightguide section is prefabricated in bent form, in particular it is precast.

* * * * *